US008113056B2

(12) United States Patent
Drake, Jr. et al.

(10) Patent No.: US 8,113,056 B2
(45) Date of Patent: Feb. 14, 2012

(54) MID-IR LASER FOR GENERATION OF ULTRASOUND USING A $CO_2$ LASER AND HARMONIC GENERATION

(75) Inventors: Thomas E. Drake, Jr., Fort Worth, TX (US); Marc Dubois, Keller, TX (US); Peter W. Lorraine, Niskayuna, NY (US); John B. Deaton, Jr., Niskayuna, NY (US); Robert Filkins, Niskayuna, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 190 days.

(21) Appl. No.: 12/121,012

(22) Filed: May 15, 2008

(65) Prior Publication Data

US 2009/0282919 A1    Nov. 19, 2009

(51) Int. Cl.
*G01N 29/04* (2006.01)
*G01N 21/41* (2006.01)

(52) U.S. Cl. .......................................... 73/643; 73/657

(58) Field of Classification Search ............... 73/643, 73/655, 656, 657
See application file for complete search history.

(56) References Cited

U.S. PATENT DOCUMENTS

| | | | | |
|---|---|---|---|---|
| 5,982,482 | A * | 11/1999 | Nelson et al. | 356/237.1 |
| 6,176,135 | B1 | 1/2001 | Dubois et al. | |
| 7,117,134 | B2 * | 10/2006 | Dubois et al. | 703/5 |
| 7,387,027 | B2 * | 6/2008 | Choi et al. | 73/668 |

FOREIGN PATENT DOCUMENTS

| | | |
|---|---|---|
| EP | 1 228 501 | 2/2001 |
| WO | 01/07906 A1 | 2/2001 |

OTHER PUBLICATIONS

Dubois et al., "Experimental verification of the effects of optical wavelength on the amplitude of laser generated ultrasound in polymer-matrix composites", Ultrasonics 40 (2002), pp. 809-812.
Dubois et al., "Experimental comparison between optical spectroscopy and laser-ultrasound generation in polymer-matrix composites", Applied Physics Letter, vol. 79, No. 12, Sep. 17, 2001, pp. 1813-1815.
Dubois et al., "Progress on the Development of an Advanced Laser Ultrasound Generation Source for Inspecting Polymer-Matrix Composites", CP615, Review of Quantitative Nondestructive Evaluation vol. 21, ed. by D.O. Thompson and D. E. Chimenti, American Institute of Physics (2002), pp. 300-307.
Carbon dioxide laser, http://en.wikipedia.org/wiki/CO2_laser; Mar. 6, 2008, 3 pages.
International Search Report and Written Opinion, PCT/US2009/043930, dated Aug. 11, 2009.

(Continued)

*Primary Examiner* — Hezron E Williams
*Assistant Examiner* — Rose M Miller
(74) *Attorney, Agent, or Firm* — Bracewell & Giuliani LLP

(57) ABSTRACT

A mid infrared range laser source for ultrasound inspection having a high energy laser coupled with one or more harmonic generation devices. The high energy laser may be a $CO_2$ laser and tuned to emit laser light at a single wavelength. The harmonic generation devices convert the laser beam into the mid infrared range for optimal ultrasound inspection.

24 Claims, 1 Drawing Sheet

OTHER PUBLICATIONS

Edwards et al., "Laser Generated Ultrasound: Efficiency and Damage Thresholds in Carbon Fibre Reinforced Composites", IEE Proc.-Sci. Meas. Technol., vol. 148, No. 4, Jul. 2001, pp. 139-142. XP-002539319.

Huang et al., "Second Harmonic Generation in Tunable, Tea CO2 Laser", Proceedings of SPIE vol. 4891, 2003, pp. 377-383. XP002539320.

* cited by examiner

MID-IR LASER FOR GENERATION OF ULTRASOUND USING A CO₂ LASER AND HARMONIC GENERATION

BACKGROUND

1. Field of Invention

The invention relates generally to the field of non-destructive testing. More specifically, the present invention relates to a system to create a mid-range infrared generation laser beam using a carbon dioxide ($CO_2$) laser and generating a harmonic of the $CO_2$ laser output.

2. Description of Prior Art

Recent developments in creating composite materials have expanded the use of composite materials into a wide variety of applications. Because of its high strength and durability combined with its low weight, composites are replacing metals and metal alloys as the base material for certain load bearing components. For example, composites are now commonly used as a material for body parts and structure in vehicles such as automobiles, watercraft, and aircraft. However, to ensure composite mechanical integrity, strict inspections are required. The inspections are typically required upon fabrication of a component made from a composite and periodically during the life of the component.

Laser ultrasound is one example of a method of inspecting objects made from composite materials. The method involves producing ultrasonic vibrations on a composite surface by radiating a portion of the composite with a pulsed generation laser. A detection laser beam is directed at the vibrating surface and scattered, reflected, and phase modulated by the surface vibrations to produce phase modulated light. Collection optics receives the phase modulated laser light and directs it for processing. Processing is typically performed by an interferometer coupled to the collection optics. Information concerning the composite can be ascertained from the phase modulated light processing, the information includes the detection of cracks, delaminations, porosity, and fiber information. Currently known laser ultrasonic detections systems used for analyzing composite target objects have a limited energy and repetition rate (frequency). At a target surface, typical laser beam energy values for a mid infrared generation laser beam are about 10 milli-Joules (mJ) with a corresponding pulsed frequency of about 10 Hertz (Hz).

SUMMARY OF INVENTION

Disclosed herein is a method of ultrasonic testing a target object using a high energy generation laser beam comprising, providing a CO2 laser beam, producing a harmonic of the CO2 laser beam, directing the CO2 laser beam harmonic to the target object, thermo-elastically exciting a surface of the target object to produce ultrasonic displacements on the target object, and measuring the ultrasonic displacements. The CO2 harmonic may be a second or a third harmonic. An optical fiber may be coupled to the CO2 laser beam. The CO2 laser beam harmonic energy at the target object may be at least 50 milli-Joules, at least 75 milli-Joules, or at least 100 milli-Joules. The CO2 laser beam pulsed frequency at the target object may be at least 200 Hz or at least 400 Hz. The CO2 laser beam harmonic wavelength may range from about 3 microns to about 4 microns or be about 3.2 microns.

Also disclosed herein is an ultrasonic detection system. In one embodiment the system comprises, a CO2 laser, a harmonic beam generation system, a CO2 laser beam emitted from CO2 laser and directed to the harmonic beam generation system; and a harmonic beam of the CO2 laser beam emitted from the harmonic beam generation system and directed to a target object. In an embodiment, the harmonic beam thermo-elastically expands a portion of the target object thereby producing displacements on the target surface, the detection system further comprises a detection beam directed at the displacements, wherein the detection beam is phase modulated and reflected by the displacements. The harmonic generation system may be a second harmonic generator or a third harmonic generator. The CO2 laser beam energy emitted from the CO2 laser can be at least about 4.5 Joules or at least about 1 Joule. The harmonic laser beam energy at the target can be at least about 50 milli-Joules or at least about 100 milli-Joules. The harmonic laser beam wavelength can range from about 3 microns to about 4 microns or can be about 3.2 microns.

BRIEF DESCRIPTION OF DRAWINGS

Some of the features and benefits of the present invention having been stated, others will become apparent as the description proceeds when taken in conjunction with the accompanying drawings, in which.

Figure 1:
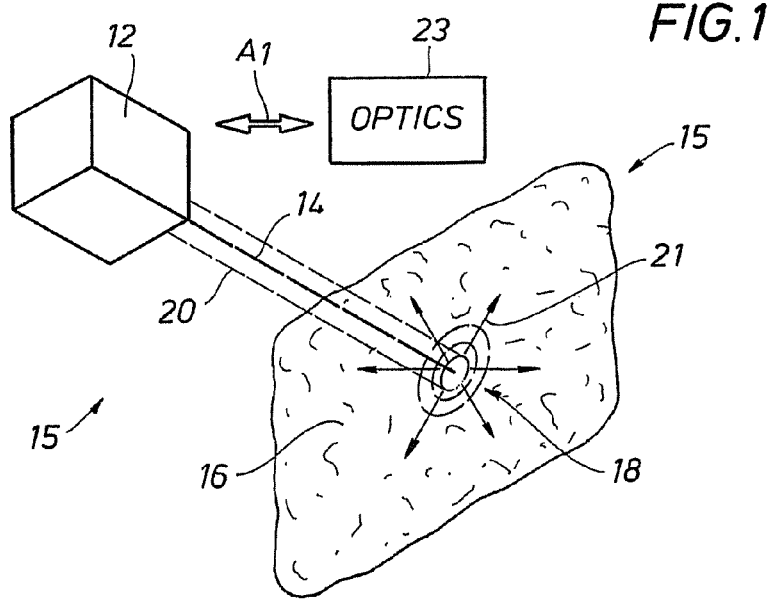
FIG. 1 is a schematic representation of a laser ultrasonic detection system.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The present invention will now be described more fully hereinafter with reference to the accompanying drawings in which embodiments of the invention are shown. This invention may, however, be embodied in many different forms and should not be construed as limited to the illustrated embodiments set forth herein; rather, these embodiments are provided so that this disclosure will be thorough and complete, and will fully convey the scope of the invention to those skilled in the art. Like numbers refer to like elements throughout. For the convenience in referring to the accompanying figures, directional terms are used for reference and illustration only. For example, the directional terms such as "upper", "lower", "above", "below", and the like are being used to illustrate a relational location.

It is to be understood that the invention is not limited to the exact details of construction, operation, exact materials, or embodiments shown and described, as modifications and equivalents will be apparent to one skilled in the art. In the drawings and specification, there have been disclosed illustrative embodiments of the invention and, although specific terms are employed, they are used in a generic and descriptive sense only and not for the purpose of limitation. Accordingly, the invention is therefore to be limited only by the scope of the appended claims.

FIG. 1 provides a side perspective view of one embodiment of a laser ultrasonic detection system 10. The detection system 10 comprises a laser ultrasonic unit 12 formed to emit a generation beam 14 and directed to an inspection target 15. The generation beam 14 contacts the inspection target 15 on an inspection surface 16. The generation beam 14 thermo-elastically expands the inspection surface 16 to produce corresponding wave displacements 18 on the inspection surface 16. In one embodiment, the generation beam 14 is a pulsed laser configured to produce the wave displacements 18 on the inspection surface 16. A detection beam 20 is also illustrated emanating from the laser ultrasonic unit 12 and is shown coaxial around the generation beam 14. Although emanating from the same laser ultrasonic unit 12, the detection and generation beams (14, 20) are generated by different sources. However, the detection beam 20 may optionally originate from a different unit as well as a different location. As is known, the detection beam 20 comprises a detection wave that is scattered, reflected, and phase modulated upon contact with the wave displacements 18 to form phase modulated light 21. The phase modulated light 21 from the detection beam 20 is then received by collection optics 23 and processed to determine information about the inspection target 15. The generation and detection beams (14, 20) may be scanned across the target 15 to obtain information regarding the entire surface 16. A mechanism (not shown) used to scan the beams (14, 20) may be housed within the laser ultrasonic unit 12. A processor (not shown) for controlling the mechanism and optionally for processing the data recorded by the collection optics, may also be housed in the laser ultrasonic unit 12. The collection optics 23 are shown separate from the laser ultrasonic unit 12 and in communication with the laser ultrasonic unit 12 through the arrow Al, however the collection optics may be included with the laser ultrasonic unit 12.

Figure 2:
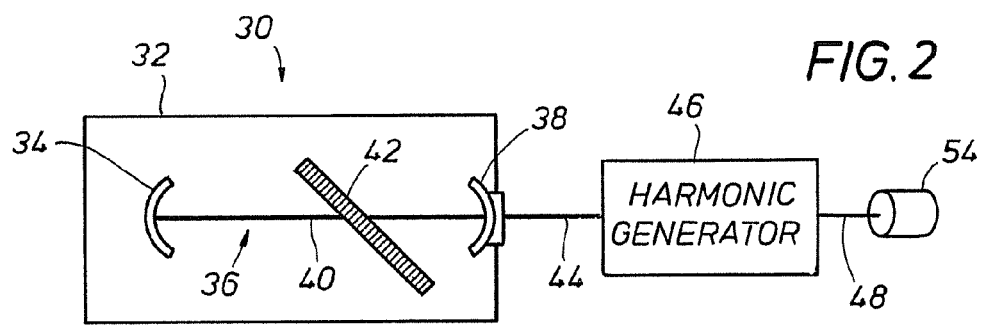
FIG. 2 is a schematic view of a mid range infrared ultrasonic laser source in accordance with the present disclosure.

With reference now to FIG. 2, one example of a mid infrared laser system 30 is shown in a schematic view. The system 30 produces a mid IR beam that may be used as the generation beam 14 of FIG. 1. The mid IR laser system 30 comprises a $CO_2$ laser 32 used to form a $CO_2$ laser beam 44. Schematically illustrated within the $CO_2$ laser 32 is a mirror 34 and an output coupler 38 operatively disposed within the laser 32. A cavity 36 is provided between the mirror 34 and the output coupler 38. Energy input into the $CO_2$ laser 32, combined with the operative coupling of the mirror and a reflective surface of the output coupler 38, generate a beam between these two reflective surfaces. A diffraction grating 42 is provided within the cavity 36 and configured to permit therethrough photons having a particular wavelength. The diffraction grating 42 within the cavity 36 thus forms a single wavelength beam 40 in the cavity 36.

Some photons of the single wavelength beam 42 escape from the $CO_2$ laser 32 through the output coupler 38 to form a $CO_2$ beam 44. The embodiment of FIG. 2 illustrates a harmonic generator 46 disposed in the path of the $CO_2$ beam 44. The harmonic generator 46 converts the $CO_2$ beam 44 to a harmonic to create a harmonic beam 48 passing from the harmonic generator 46. Optionally, an optical fiber 54 is shown receiving the harmonic beam 48 for generation and direction of the generation beam 14. The harmonic beam 48 may be at the second harmonic of the fundamental wavelength with $CO_2$ beam 44. Optionally, the harmonic beam 48 may be at the third harmonic, or some other harmonic of the fundamental wavelength of the $CO_2$ beam 44.

Figure 3:
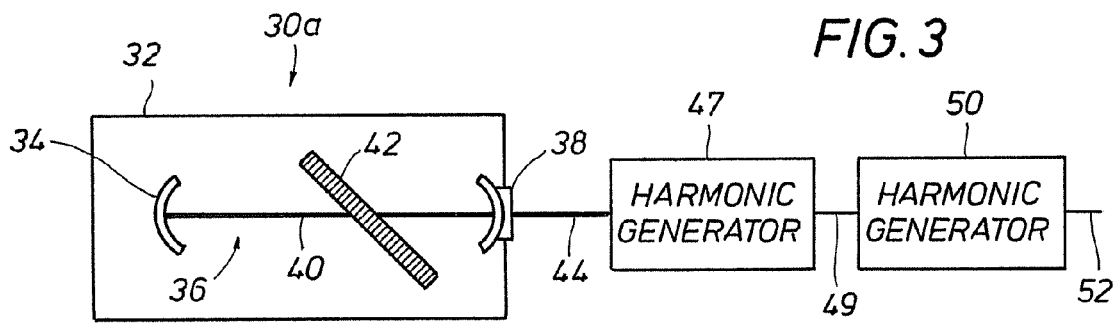
FIG. 3 is a schematic view of a mid range infrared ultrasonic laser source in accordance with the present disclosure.

FIG. 3 provides an alternate embodiment of a mid IR laser system 30a wherein the $CO_2$ beam 44 is conditioned by more than one harmonic generator. In FIG. 3, the $CO_2$ beam 44 is directed to a second harmonic generator 47 that changes the $CO_2$ beam 44 to a second harmonic thereby forming the second harmonic beam 49. The second harmonic beam 49 is directed to a third harmonic generator 50 that emits a third harmonic beam 52 having a wavelength substantially equal to the third harmonic of the fundamental wavelength of the $CO_2$ beam 44. The embodiment of FIG. 3 is not limited to the two harmonic generators shown, but can include additional harmonic generators disposed in the path of the laser beam. The third harmonic beam 52 can also be used as the generation beam 14 of FIG. 1 emitted from the laser ultrasonic source 12. The third harmonic generator 50 can produce the third harmonic of the $CO_2$ laser beam 44 either by direct conversion or can convert the fundamental wavelength and mix it with the second harmonic wavelength to form the third harmonic of the $CO_2$ laser beam fundamental wavelength.

In one embodiment of a detection or testing system disclosed herein, the $CO_2$ laser beam can be harmonically processed to have a wavelength of between about 3 microns up to about 5.5 microns. Optionally, the $CO_2$ laser beam can have a wavelength in the entire mid infrared range. Optionally, the $CO_2$ laser beam can have a wavelength of from about 3 microns to about 4 microns. Optionally, the $CO_2$ laser beam can have a wavelength of about 3.2 microns.

One of the many advantages of employing a $CO_2$ laser for the formation of a laser beam used for ultrasonic displacement testing of target objects is the high energy available with the $CO_2$ laser. The increased energy correspondingly produces displacements with higher amplitudes; this provides more discrete measurements and precision in the recorded testing data.

The $CO_2$ laser produces a beam whose wavelength extends from about 9 microns to about 11 microns and has a usual wavelength of about 10.6 microns. Laser beams at this wavelength have a relatively shallow optical depth when directed to composite materials which concentrates laser beam energy at a composite surface. Composites can be damaged by $CO_2$ lasers if too much energy is applied to the surface or the beam is allowed to contact the surface for a protracted period of time. However, laser beams in the mid IR range, i.e., from about 3 microns to about 4 microns, have an increased optical depth thereby allowing more laser energy into the composite surface without the danger of surface ablations. Thus, an additional advantage of laser ultrasonic testing of a composite with a $CO_2$ beam harmonic is that the laser beam can be used having a higher energy level which corresponds to higher amplitude displacements on the testing surface.

The $CO_2$ laser 30 can be designed to emit its corresponding laser beam 44 at various values of energy. Values of at least one Joule up to and in excess of about 4.5 Joules may be realized for a $CO_2$ laser 30 design. Additionally, the $CO_2$ laser 30 can be configured such that its corresponding beam 44 has an energy value of any number between 1 Joule and 4.5 Joules. Thus, depending on the conversion efficiency of the harmonic generators, the energy value of the generation beam contacting the target surface can be multiples of the current value of 10 milli-Joules of currently available ultrasonic laser testing systems. Thus, the method and system disclosed herein can provide a generation laser beam having a value at target surface contact of at least about 50 milli-Joules, at least about 75 milli-Joules, at least about 100 milli-Joules, and at least about 300 milli-Joules. Additionally, the frequency of the generation beam 14 can be higher than the 10 Hz currently available. The pulsed frequency values can be at least about 100 Hz, at least about 200 Hz, at least about 300 Hz, at least about 400 Hz, at least about 500 Hz, and at least up to about 1000 Hz.

In one embodiment, the harmonic generators (46, 47, 50) may be crystals and may be critical phase matched or quasi-phase matched configurations. In one example, the crystals may be made from the following compounds: $AgGaS_2$, $AgGaSe_2$, GaAs, GaSe, $ZnGeP_2$(ZGP), $AgGa1\text{-}xlnxSe_2$, $Tl_3AsSe3$(TAS), $CdGeAs_2$(CGA), and combinations thereof.

An additional advantage of using a harmonic laser beam formed by a $CO_2$ laser for laser ultrasonic testing is the harmonic laser beam is less likely to damage a composite surface during testing of the target object. Additionally, the high energy of the $CO_2$ laser can be used to create higher and more readily measurable displacements within the target surface. Yet another advantage is the ability of coupling the $CO_2$ laser beam with fiber optics for enhanced transmissibility of the laser beam.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

What is claimed is:

1. A method of ultrasonic testing a target object made of composite materials using a high energy generation laser beam, the method comprising:
   providing a $CO_2$ laser beam having an energy of from about 1 Joule to about 4.5 Joule and a fundamental wavelength of from about 9 microns to about 11 microns;
   directing the fundamental wavelength of the $CO_2$ laser beam to a harmonic generator formed of crystals;
   producing a selected harmonic wavelength of the fundamental wavelength of the $CO_2$ laser beam using the harmonic generator, the selected harmonic wavelength having an energy in a range of at least about 50 milli-Joules and a wavelength of from about 3 microns to about 4 microns;
   directing pulses of the selected harmonic wavelength of the $CO_2$ laser beam to the target object, the pulses being at a pulsed frequency in the range from about 100 Hz to 1000 Hz;
   thermo-elastically exciting a surface of the target object to produce ultrasonic displacements on the target object; and
   measuring the ultrasonic displacements.

2. The method of claim 1 wherein the step of producing the selected harmonic wavelength comprises producing a second harmonic wavelength of the fundamental wavelength of the $CO_2$ laser beam with the harmonic generator.

3. The method of claim 2 wherein the step of producing the selected harmonic wavelength comprises producing a third harmonic wavelength of the fundamental wavelength of the $CO_2$ laser beam with an additional harmonic generator.

4. The method of claim 1, further comprising coupling the selected harmonic wavelength of the $CO_2$ laser beam to an optical fiber before directing the selected harmonic wavelength of the $CO_2$ laser beam to the target object.

5. The method of claim 2, wherein the step of producing the selected harmonic wavelength further comprises converting the fundamental wavelength to a converted wavelength with an additional harmonic generator, and mixing the converted wavelength with the second harmonic wavelength to form the selected harmonic, wavelength of the $CO_2$ laser beam.

6. The method of claim 1, wherein the selected harmonic wavelength of the $CO_2$ laser beam has an energy of at least 100 milli-Joules.

7. The method of claim 1, wherein the selected harmonic wavelength of the $CO_2$ laser beam has an energy of at least 300 milli-Joules.

8. The method of claim 1, wherein the laser beam pulsed frequency is at least about 500 Hz.

9. The method of claim 1, wherein the $CO_2$ laser beam pulsed frequency is at least 200 Hz.

10. The method of claim 1, wherein the $CO_2$ laser beam pulsed frequency is at least 400 Hz.

11. The method of claim 3, wherein producing the third harmonic wavelength comprises:
   directing the second harmonic wavelength to the additional harmonic generator, and converting the second harmonic wavelength to the third harmonic wavelength using the additional harmonic generator.

12. An ultrasonic detection system comprising:
   a $CO_2$ laser;
   a harmonic beam generation system formed of crystals;
   a CO, laser beam emitted from $CO_2$ laser, the $CO_2$ laser beam having an energy of from about 1 Joule to about 4.5 Joule and a fundamental wavelength of from about 9 microns to about 11 microns and directed to the harmonic beam generation system; and
   a selected harmonic wavelength beam emitted from the harmonic beam generation system that is at a selected harmonic wavelength of the fundamental wavelength of the $CO_2$ laser beam, the selected harmonic wavelength beam having an energy of at least about 50 milli-Joules and having a wavelength of from about 3 microns to about 5.5 microns; and
   the selected harmonic wavelength beam being directed in pulses at a pulsed frequency from about 100 to 1000 Hz to a surface of a target object for determining information about the surface of the target object.

13. The ultrasonic detection system of claim 12, wherein the selected harmonic wavelength beam thermo-elastically expands a portion of the target object thereby producing displacements on the target surface, the detection system further comprising a detection beam directed at the displacements, wherein the detection beam is phase modulated and reflected by the displacements.

14. The ultrasonic detection system of claim 12 wherein the harmonic generation system comprises a harmonic generator for producing a second harmonic wavelength of the fundamental wavelength and another harmonic generator for producing a third harmonic wavelength of the fundamental wavelength.

15. The ultrasonic detection system of claim 12 wherein the harmonic generation system comprises a harmonic generator for producing a second harmonic wavelength of the fundamental wavelength, and an additional harmonic generator for producing an additional harmonic wavelength of the fundamental wavelength, and the selected harmonic wavelength beam comprises a mixture of the additional harmonic wavelength and the second harmonic wavelength.

16. The ultrasonic detection system of claim 12 wherein the energy of the harmonic wavelength beam is at least about 100 milli-Joules.

17. The ultrasonic detection system of claim 12 wherein the enemy of the harmonic wavelength beam is at least about 300 milli-Joules.

18. The ultrasonic detection system of claim 12 wherein the pulsed frequency is at least about 400 Hz.

19. The ultrasonic detection system of claim 12 wherein the pulsed frequency is at least about 500 Hz.

20. The ultrasonic detection system of claim 12 wherein the harmonic laser beam wavelength is from about 3 microns to about 4 microns.

21. The ultrasonic detection system of claim 12 wherein the harmonic laser beam wavelength is about 3.2 microns.

22. A method of ultrasonic testing a target object made of composite materials using a high energy generation laser beam, the method comprising:
  (a) providing a $CO_2$ laser beam having an energy of from about 1 Joule to about 4.5 Joule and a fundamental wavelength of from about 9 microns to about 11 microns;
  (b) directing the fundamental wavelength of the $CO_2$ laser beam to a harmonic generator formed of crystals;
  (c) producing a second harmonic wavelength of the fundamental wavelength of the $CO_2$ laser beam using the harmonic generator;
  (d) producing a third harmonic wavelength of the fundamental wavelength of the $CO_2$ laser beam using an additional harmonic generator formed of crystals, the third harmonic wavelength having an energy in a range of at least about 50 milli-Joules and a wavelength of from about 3 microns to about 4 microns;
  (e) directing pulses of the third harmonic wavelength of the $CO_2$ laser beam to the target object, the pulses being at a pulsed-frequency in the range from about 100 Hz to 1000 Hz;
  (f) thermo-elastically exciting a surface of the target object to produce ultrasonic displacements on the target object; and
  (g) measuring the ultrasonic displacements.

23. The method according to claim 22, wherein step (d) comprises:
  directing the second harmonic wavelength to the additional harmonic generator and converting the second harmonic wavelength to the third harmonic wavelength using the additional harmonic generator.

24. The method according to claim 22, where step (d) comprises:
  converting the fundamental wavelength to a converted wavelength with the additional harmonic generator, and mixing the converted wavelength with the second harmonic wavelength to form the third harmonic wavelength.

* * * * *